United States Patent
Yu

(10) Patent No.: US 10,413,582 B2
(45) Date of Patent: Sep. 17, 2019

(54) PHARMACEUTICAL COMPOSITION FOR TREATING ECZEMA AND METHOD FOR PREPARATION THEREOF

(71) Applicant: ZHEJIANG STRONG PHARMACEUTICAL CO., LTD., Hangzhou, Zhejiang (CN)

(72) Inventor: Luping Yu, Zhejiang (CN)

(73) Assignee: ZHEJIANG STRONG PHARMACEUTICAL CO., LTD., Hangzhou, Zhejiang (CN)

( * ) Notice: Subject to any disclaimer, the term of this patent is extended or adjusted under 35 U.S.C. 154(b) by 0 days.

(21) Appl. No.: 15/825,884

(22) Filed: Nov. 29, 2017

(65) Prior Publication Data

US 2018/0147249 A1 May 31, 2018

(30) Foreign Application Priority Data

Nov. 29, 2016 (CN) .......................... 2016 1 1071712

(51) Int. Cl.

| | | |
|---|---|---|
| *A61K 36/9068* | (2006.01) |
| *A61K 9/16* | (2006.01) |
| *A61K 36/28* | (2006.01) |
| *A61K 36/539* | (2006.01) |
| *A61K 36/65* | (2006.01) |
| *A61K 36/708* | (2006.01) |
| *A61K 36/8945* | (2006.01) |
| *A61K 36/899* | (2006.01) |
| *A61K 36/9062* | (2006.01) |
| *A61K 36/9064* | (2006.01) |
| *A61K 9/00* | (2006.01) |
| *A61K 9/20* | (2006.01) |
| *A61K 9/48* | (2006.01) |

(52) U.S. Cl.
CPC ........ *A61K 36/9068* (2013.01); *A61K 9/0095* (2013.01); *A61K 9/1652* (2013.01); *A61K 9/2068* (2013.01); *A61K 9/4866* (2013.01); *A61K 36/28* (2013.01); *A61K 36/539* (2013.01); *A61K 36/65* (2013.01); *A61K 36/708* (2013.01); *A61K 36/899* (2013.01); *A61K 36/8945* (2013.01); *A61K 36/9062* (2013.01); *A61K 36/9064* (2013.01); *A61K 2236/331* (2013.01); *A61K 2236/333* (2013.01); *A61K 2236/37* (2013.01); *A61K 2236/39* (2013.01); *A61K 2236/51* (2013.01); *A61K 2236/53* (2013.01)

(58) Field of Classification Search
None
See application file for complete search history.

(56) References Cited

FOREIGN PATENT DOCUMENTS

| | | |
|---|---|---|
| CN | 101297956 A | 11/2008 |
| CN | 101642546 A | 2/2010 |
| CN | 102058855 A | 5/2011 |
| CN | 103100075 A | 5/2013 |
| CN | 103656561 A | 3/2014 |
| CN | 104548037 A | 4/2015 |
| CN | 104645258 A | 5/2015 |
| CN | 105056140 A | 11/2015 |
| CN | 105288436 A | 2/2016 |
| CN | 105920220 A | 9/2016 |
| CN | 106074758 A | 11/2016 |
| KR | 20150088414 A | 8/2015 |
| WO | WO9600078 A1 | 1/1996 |
| WO | WO2012036446 A2 | 3/2012 |

OTHER PUBLICATIONS

Hui-Lei Wan; "Study on effect of Traditional Chinese Medicine Jianpi Chushi decoction and ointment on chronic eczema"; Asian Pacific Journal of Tropical Medicine 2016; 9(9): pp. 920-923.
Hye-Sun Lim et al; "Effect of Alpinia katsumadai Hayata on House DustMite-Induced Atopic Dermatitis in NC/NgaMice"; Evidence-Based Complementary and Alternative Medicine; vol. 2012, pp. 1-9.

*Primary Examiner* — Qiuwen Mi
(74) *Attorney, Agent, or Firm* — Muncy, Geissler, Olds & Lowe, P.C.

(57) ABSTRACT

A pharmaceutical composition for treating eczema is disclosed. The pharmaceutical composition includes, by weight, 2 to 6 parts of Dried Rhizoma Zingiberis Officinalis, 2 to 6 parts of Paeonia Lactiflora, 1 to 4 parts of Fructus Amomi, 0.5 to 3 parts of Semen Alpiniae Katsumadai, 0.5 to 3 parts of Inula helenium, 0.5 to 3 parts of Radix Et Rhizoma Rhei and 0.5 to 3 parts of Rhizoma Dioscoreae. The components of the pharmaceutical composition synergistically cooperate to clear and disinhibit the liver and gallbladder and clear away damp heat from the body. The pharmaceutical composition can be used to treat skin eczema symptoms caused by metabolic disorders of the liver and gallbladder functions. A method for preparing the pharmaceutical composition is also disclosed.

9 Claims, No Drawings

PHARMACEUTICAL COMPOSITION FOR TREATING ECZEMA AND METHOD FOR PREPARATION THEREOF

TECHNICAL FIELD

The present invention relates to compound traditional Chinese medicine (TCM) preparations and, in particular, to a pharmaceutical composition for treating eczema and a method for preparing such a pharmaceutical composition.

BACKGROUND

Eczema, also known as atopic eczema or atopic dermatitis, is an inflammatory, allergic skin disease commonly and frequently encountered in dermatology. Clinically, eczema is mainly manifested as recurrent itchiness and symmetrically distributed pleomorphic lesions and characterized in symmetrically distributed pleomorphic skin lesions, severe itchiness, a tendency to oozing, recurrence, refractoriness, proneness to chronicity and persistence, etc. Histological characteristics include edema between epidermal cells, accompanied by varying degrees of acanthosis and lymphohistiocytic infiltration around superficial vessels.

At present, the pathogenesis of eczema has not yet been fully elucidated in Western medicine. Well-accepted possible causes mainly include allergies, skin barrier defects, pathogenic microbial colonization, inflammatory mediator release, genetic polymorphisms or mutations and other environmental factors. Eczema can be specified as acute, sub-acute or chronic, depending upon the appearance of lesions and may induce *Staphylococcus aureus* skin infections, herpes simplex virus infections, warts, infectious plaques or other conditions.

Eczema can endanger the lives and health of patients. Patients with acute or chronic eczema often suffer from erosions caused by scratching, which are prone to secondary infections that may lead to pustules and local swollen lymph nodes. Chronic eczema can lead to thickened, moss-like, local skin lesions with a protracted course. Some patients may develop life-threatening systemic diseases such as serious liver and kidney damage due to excessive medication throughout the protracted course of treatment.

The impact of eczema on patients is not limited to the physical pain and suffering, but more lies in degrading their quality of life (QOL). Rash and severe itching may inhibit the patient's normal life and work and lead to lack of sleep. Generally, a patient with eczema has a probability of 60% of sleep disorders and even higher during onset of the disease. Another reason for QOL degradation due to eczema is dietary restrictions. Other consequences of eczema include listlessness, irritability and other mental disorders resulting from prolonged treatment, impaired appearance due to papules, papules, blisters, oozing, erosions, scalp scabs, pigmentation of eczema lesions, and psychological pressures and poor mental health because of some characteristics of the disease such as unidentifiable causes and allergens, proneness to recurrence and a protracted course.

In Western medicine, eczema is typically treated following the principles of controlling skin inflammation, relieving itching, delaying and mitigating progression, recovering or strengthening the skin barrier function and improving and enhancing patient QOL based on patients' individual needs while comprehensively considering their age, severity, lesion site, infection, past treatment and other conditions.

In general, the treatment is medical or surgical and involves the use of H1 receptor antagonists (antihistamines), non-specific anti-allergic drugs, corticosteroids, immunomodulators or antibiotics. Most of these drugs, however, cannot fundamentally eradicate the disease but can only temporarily suppress its onset and relieve its symptoms at the cost of many side effects, for example, lethargy, drowsiness, dry mouth, vomiting, diarrhea, constipation, urinary retention and so on arising from the use of antihistamines. Use of corticosteroids can cause obesity, hirsutism, acnes, hyperglycemia, hypertension, hypernatremia, edema, hypokalemia, menstrual disorders, osteoporosis, aseptic bone necrosis, gastric and duodenal ulcers and other complications, addiction and exacerbation after withdrawal. Clinically, there are many patients who fear the use of hormones. In such cases, the treatment will be affected due to a limited choice of mediations and poor patient compliance.

SUMMARY OF THE INVENTION

In view of the above-discussed shortcomings of Western medicine in the treatment of eczema, the present invention discloses a pharmaceutical composition for treating eczema. Also disclosed is a method for preparing the pharmaceutical composition, which allows easy preparation of the pharmaceutical composition with simple conditions and is safe, reliable and suitable for industrial production.

The pharmaceutical composition for treating eczema, includes, by weight, 2 to 6 parts of Dried Rhizoma Zingiberis Officinalis, 2 to 6 parts of Paeonia Lactiflora, 1 to 4 parts of Fructus Amomi, 0.5 to 3 parts of Semen Alpiniae Katsumadai, 0.5 to 3 parts of Inula helenium, 0.5 to 3 parts of Radix Et Rhizoma Rhei and 0.5 to 3 parts of Rhizoma Dioscoreae.

Preferably, the pharmaceutical composition may include, by weight, 2 to 4 parts of Dried Rhizoma Zingiberis Officinalis, 2 to 4 parts of Paeonia Lactiflora, 1 to 3 parts of Fructus Amomi, 0.5 to 2 parts of Semen Alpiniae Katsumadai, 0.5 to 2 parts of Inula helenium, 0.5 to 2 parts of Radix Et Rhizoma Rhei and 0.5 to 2 parts of Rhizoma Dioscoreae.

More preferably, the pharmaceutical composition may include, by weight, 3 parts of Dried Rhizoma Zingiberis Officinalis, 3 parts of Paeonia Lactiflora, 2 parts of Fructus Amomi, 1 part of Semen Alpiniae Katsumadai, 1 part of Inula helenium, 1 part of Radix Et Rhizoma Rhei and 1 part of Rhizoma Dioscoreae.

In one embodiment, the pharmaceutical composition may include, in every 12 g of the pharmaceutical composition, 3 g of Dried Rhizoma Zingiberis Officinalis, 3 g of Paeonia Lactiflora, 2 g of Fructus Amomi, 1 g of Semen Alpiniae Katsumadai, 1 g of Inula helenium, 1 g of Radix Et Rhizoma Rhei and 1 g of Rhizoma Dioscoreae.

In another embodiment, the pharmaceutical composition for treating eczema may further include, by weight, 2 to 6 parts of Fructus Aurantii Immaturus, 0.5 to 3 parts of Radix Scutellariae Bai-calensis and 0.5 to 3 parts of Caulis Bambusae in Taeniam.

Further, the pharmaceutical composition may assume a form of oral solutions, tablets, capsules, pills granules or dropping pills.

The method for preparing the pharmaceutical composition includes the steps of:

step A) subjecting a first group of medicine materials including Dried Rhizoma Zingiberis Officinalis, Fructus Amomi, Semen Alpiniae Katsumadai, and Inula helenium to three reflux extraction processes each lasting for 1-2 hours and using a 50%-80% ethanol solution as an extraction medium which has a number of units of volume (L) 6 times a number of units of a total weight (Kg) of the first group of medicine materials;

step B) combining and filtering the ethanol solutions used in the three reflux extraction processes to obtain a first filtrate and concentrating the first filtrate under a reduced pressure, concurrently with recovery of the ethanol solutions, until relative density of the concentrated first filtrate comes to 1.05-1.15;

step C) subjecting a second group of medicine materials including Paeonia Lactiflora, Radix Et Rhizoma Rhei and Rhizoma Dioscoreae to three boiling processes each lasting for 1-2 hours and using water with a weight 8-12 times a total weight of the second group of medicine materials as a boil medium;

step D) combining and filtering the water used in the three boiling processes to obtain a second filtrate, mixing the second filtrate with the first filtrate obtained from step B to obtain a first mixture, concentrating the first mixture until a weight of the first mixture becomes 1-3 times a total weight of the first and second groups of medicine materials and keeping the concentrated first mixture at room temperature for 24 hours; and step E) filtering and centrifuging a supernatant of the concentrated first mixture to obtain a centrifugate, concentrating the centrifugate into an extract with a relative density of 1.10-1.35, and drying the extract to produce the pharmaceutical composition.

Optionally, the method may further include a step of: step F) homogeneously mixing the pharmaceutical composition with starch to obtain a second mixture, forming the second mixture into granules and filling the granules in packs.

Preferably, in step B, the first filtrate is concentrated at 75° C. until the relative density of the concentrated first filtrate comes to 1.05-1.15.

Preferably, in step E, the centrifugate may be concentrated at 75° C. into the extract with a relative density of 1.10-1.35, wherein the extract is dried with microwaves to produce the pharmaceutical composition.

Optionally, in step A, the first group of medicine materials may further include 2 to 6 parts of Fructus Aurantii Immaturus and 0.5 to 3 parts of Radix Scutellariae Bai-calensis; and in step C, the second group of medicine materials may further include 0.5 to 3 parts of Caulis Bambusae in Taeniam.

Compared with the prior art, the invention has the advantages as follows:

Clinical trials have found that the seven Chinese medicine (TCM) materials in the pharmaceutical composition of the present invention, i.e., Dried Rhizoma Zingiberis Officinalis, Paeonia Lactiflora, Fructus Amomi, Semen Alpiniae Katsumadai, Inula helenium, Radix Et Rhizoma Rhei and Rhizoma Dioscoreae, synergistically cooperate to clear and disinhibit the liver and gallbladder and clear away damp heat from the body, and that the pharmaceutical composition can be used to treat skin eczema symptoms, in particular in infants, young children and adolescents, caused by metabolic disorders of the liver and gallbladder functions, transformation of enduring depression into heat and disorders of transportation and transformation, such as skin redness, rash, edema, itching and dry skin. The pharmaceutical composition treats the disease from its internal root causes by regulating the liver and gallbladder functions and purging stagnant damp heat in the body. It is capable of relieving itching, clearing dampness and heart and facilitating self-healing of skin. In addition, the pharmaceutical composition is safe, has a good effect of improving eczema and solves the prior-art problems of many side effects, proneness to addiction, exacerbation after withdrawal, temporary suppression rather than eradication, severe liver or kidney damage caused by long-term medication, etc.

Further, the method allows easy preparation of the pharmaceutical composition with simple conditions and is environmental friendly, cost-effective, efficient, free of toxicity. Hence, it has a wide application foreground.

DETAILED DESCRIPTION OF EXEMPLARY EMBODIMENTS

While specific embodiments of the present invention are set forth below, the invention is not limited to these embodiments. The advantages and features of the present invention will become more apparent from the following description and the appended claims.

The present invention proposes a pharmaceutical composition for treating eczema, including, by weight, 2 to 6 parts of Dried Rhizoma Zingiberis Officinalis (Gan Jiang), 2 to 6 parts of Paeonia Lactiflora (Chi Shao), 1 to 4 parts of Fructus Amomi (Sha Ren), 0.5 to 3 parts of Semen Alpiniae Katsumadai (Cao Dou Kou), 0.5 to 3 parts of Inula helenium (Tu Mu Xiang), 0.5 to 3 parts of Radix Et Rhizoma Rhei (Da Huang) and 0.5 to 3 parts of Rhizoma Dioscoreae (Shan Yao). Such a pharmaceutical composition is safe and has a good effect of improving eczema. It solves the prior-art problems of many side effects, proneness to addiction, exacerbation after withdrawal, temporary suppression rather than eradication, severe liver or kidney damage caused by long-term medication, etc.

Gan Jiang is pungent in flavor and warm in nature. It interacts with the Spleen, Stomach, Kidney, Heart and Lung meridians to warm the spleen and stomach, restore devastated Yang, unblock channels and warm the lung to transform thin mucus. Chi Shao is bitter in flavor and slightly cold in nature. It interacts with the Liver meridian to clear heat, cool blood, dissipate blood stasis and relieve pain. Sha Ren is pungent in flavor and warm in nature. It interacts with the Spleen, Stomach and Kidney meridians to resolve dampness, whet the appetite, warm the spleen, control diarrhea, regulate the flow of Qi and prevent miscarriage. Cao Dou Kou is pungent in flavor and warm in nature. It interacts with the Spleen and Stomach meridians to dry dampness, promote the circulation of Qi, warm the spleen and stomach and relieve nausea. Tu Mu Xiang is pungent and bitter in flavor and warm in nature. It interacts with the Liver and Spleen meridians to tonify spleen and stomach, promote the circulation of Qi, relieve pain and prevent miscarriage. Da Huang is bitter in flavor and cold in nature. It interacts with the Spleen, Stomach, Large Intestine, Liver and Pericardium meridians to remove accumulation with purgation, clear heat and drain fire. Shan Yao is sweet in flavor and mild in nature. It interacts with the Spleen, Lung and Kidney meridians to nourish the spleen, stomach, lung and kidney, generate fluids and arrest seminal emission.

Preferably, the pharmaceutical composition may include, by weight, 2 to 4 parts of Gan Jiang, 2 to 4 parts of Chi Shao, 1 to 3 parts of Sha Ren, 0.5 to 2 parts of Cao Dou Kou, 0.5 to 2 parts of Tu Mu Xiang, 0.5 to 2 parts of Da Huang and 0.5 to 2 parts of Shan Yao. Such a pharmaceutical composition is safe and has a good effect of improving eczema.

Preferably, the pharmaceutical composition may include, by weight, 3 parts of Gan Jiang, 3 parts of Chi Shao, 2 parts of Sha Ren, 1 part of Cao Dou Kou, 1 part of Tu Mu Xiang, 1 part of Da Huang and 1 part of Shan Yao. Such a pharmaceutical composition is safe and has a better effect of improving eczema.

Preferably, the pharmaceutical composition may include, in every 12 g of it, 3 g of Gan Jiang, 3 g of Chi Shao, 2 g of Sha Ren, 1 g of Cao Dou Kou, 1 g of Tu Mu Xiang, 1 g of Da Huang and 1 g of Shan Yao. Such a pharmaceutical composition is safe and has the best effect of improving eczema.

Optionally, the pharmaceutical composition for treating eczema may further include, by weight, 2 to 6 parts of Fructus Aurantii Immaturus (Zhi Shi), 0.5 to 3 parts of Radix Scutellariae Bai-calensis (Huang Qin) and 0.5 to 3 parts of Caulis Bambusae in Taeniam (Zhu Ru). Wherein, Zhi Shi is bitter, pungent and sour in flavor and slightly cold in nature. It interacts with the Spleen and Stomach meridians to break stagnant Qi, purge accumulation, transform phlegm and dissipate glomus. Huang Qin is bitter in flavor and cold in nature. It interacts with the Lung, Gallbladder, Spleen, Large Intestine and Small Intestine meridians to clear heat, dry dampness, drain fire and eliminate toxicity. Zhu Ru is sweet in flavor and slightly cold in nature. It interacts with the Lung, Stomach, Heart and Gallbladder meridians to clear heat, transform phlegm, soothe irritability and relieve nausea. Thus, the effect of clearing heat can be further improved.

Preferably, the pharmaceutical composition may be prepared in the form of oral solutions, tablets, capsules, pills granules or dropping pills.

A method for preparing the pharmaceutical composition for treating eczema as defined above includes the steps as detailed below.

In step A, a first group of traditional Chinese medicine (TCM) materials, Gan Jiang, Sha Ren, Cao Dou Kou, and Tu Mu Xiang are subjected to three reflux extraction processes each lasting for 1-2 hours and using a 50%-80% ethanol solution as an extraction medium. Each ethanol solution has the number of liters (L) of its volume is 6-10 times the number of kilograms (Kg) of the total weight of the first group of TCM materials. The concentration of 50%-80% makes active ingredients in the TCM materials possible to be well extracted and dissolved in the ethanol solutions. Phase distribution equilibria during the three reflux extraction processes using the ethanol solutions each with the number of liters 6-10 times the number of kilograms of the first group of TCM materials enable good utilization of ethanol as a solvent, high extraction efficiency and more thorough extraction of the active ingredients. The duration of 1-2 hours of each extraction process enables dissolution equilibrium and hence good extraction of the active ingredients.

In step B, the ethanol solutions used in the three reflux extraction processes are combined and filtered. The filtrate is concentrated under a reduced pressure, concurrently with recovery of the ethanol, until its relative density comes to 1.05-1.15 (measured at 60° C.).

In step C, a second group of TCM materials including Chi Shao, Da Huang and Shan Yao undergo three boiling processes. In each of the processes, the second group of TCM materials are decocted in water with a weight 8-12 times their total weight for 1-2 hours. Phase distribution equilibria during the three boiling processes each using water weighing 8-12 times the second group of TCM materials enable good utilization of the solvent, high extraction efficiency and more thorough extraction of active ingredients in the second group of TCM materials. The duration of 1-2 hours of each boiling process enables dissolution equilibrium and hence good extraction of the active ingredients.

In step D, the water used in the three boiling processes is combined and filtered. The filtrate is mixed with the filtrate obtained from step B, and the mixture is concentrated until its number of liters is 1-3 times the number of kilograms of the first and second groups of TCM materials. The concentrate is kept at room temperature for 24 hours. Mixing the filtrate obtained in this step with that from step B and concentrating the mixture until its number of liters is 1-3 times the number of kilograms of the first and second groups of TCM materials and keeping the concentrate at room temperature for 24 hours enables precipitation of undesired less soluble substances contained in the filtrate from step B, such as gums, oils, fats and pigments, and of some proteins, starch and other undesired substances in the filtrate from this step. This is favorable to the subsequent separation as well as the quality of the pharmaceutical composition being prepared.

In step E, the supernatant of the concentrate is filtered and centrifuged, and the centrifugate is concentrated to an extract with a relative density of 1.10-1.35 (measured at 60° C.) which is then dried to produce the pharmaceutical composition for treat eczema. The filtration and centrifugation of the supernatant achieves further separation of the less soluble substances.

Preferably, the method may further include a step F in which the pharmaceutical composition is homogeneously mixed with starch, and the mixture is formed into granules which are filled into capsules.

Preferably, in step B, the filtrate may be concentrated at 75° C. under a reduced pressure, concurrently with recovery of the ethanol, until it has a relative density of 1.05-1.15 (measured at 60° C.).

Preferably, in step D, the mixture may be concentrated until its number of liters is 1-3 times the number of kilograms of the first and second groups of TCM materials.

Preferably, in step E, the centrifugate may be concentrated at 75° C. to the extract with a relative density of 1.10-1.35 (measured at 60° C.) which is then dried with microwaves to produce the pharmaceutical composition for treat eczema. Drying with microwaves can reduce the heating time and is therefore more desirable.

Optionally, in step A, the first group of TCM materials further includes 2 to 6 parts of Zhi Shi and 0.5 to 3 parts of Huang Qin; and in step C, the second group of TCM materials further includes 0.5 to 3 parts of Zhu Ru.

EXAMPLE 1

A pharmaceutical composition for treating eczema, including, by weight, 2 parts of Gan Jiang, 2 parts of Chi Shao, 1 part of Sha Ren, 0.5 parts of Cao Dou Kou, 0.5 parts of Tu Mu Xiang, 0.5 parts of Da Huang and 0.5 parts of Shan Yao was prepared and formed into pills.

A method for preparing the pharmaceutical composition included the steps of:

A) subjecting a first group of TCM materials including Gan Jiang, Sha Ren, Cao Dou Kou, and Tu Mu Xiang to three reflux extraction processes each lasting for 1 hour and using a 60% ethanol solution as an extraction medium which had the number of liters 6 times the number of kilograms of the first group of TCM materials;

B) combining and filtering the ethanol solutions used in the three reflux extraction processes and concentrating the filtrate under a reduced pressure, concurrently with recovery of the ethanol, until its relative density came to 1.05-1.15 (measured at 60° C.);

C) subjecting a second group of TCM materials including Chi Shao, Da Huang and Shan Yao to three boiling processes each lasting for 1 hour and using water with a weight 8 times the total weight of the second group of TCM materials as a boil medium;

D) combining and filtering the water used in the three boiling processes, mixing the filtrate with the filtrate obtained from step B, concentrating the mixture until its weight was 1.5 times the total weight of the first and second groups of TCM materials and keeping the concentrate at room temperature for 24 hours; and E) filtering and centrifuging the supernatant of the concentrate and concentrating the centrifugate into an extract with a relative density of 1.10-1.20 (60° C.), followed by drying, pulverization and formation of the extract into pills.

Optionally, Zhi Shi, Huang Qin and Zhu Ru can be added in the above pharmaceutical composition for treating eczema according to the following weight ratio: 2 parts of Gan Jiang, 2 parts of Zhi Shi, 2 parts of Chi Shao, 1 part of Sha Ren, 0.5 parts of Cao Dou Kou, 0.5 parts of Huang Qin, 0.5 parts of Tu Mu Xiang, 0.5 parts of Da Huang, 0.5 parts of Shan Yao and 0.5 parts of Zhu Ru.

Correspondingly, in the above preparation method, the method further optionally includes adding Zhi Shi and Huang Qin to the first group of TCM materials in step A and adding Zhu Ru to the second group of TCM materials in step C according to the above weight ratio.

EXAMPLE 2

A pharmaceutical composition for treating eczema, including, by weight, 4 parts of Gan Jiang, 4 parts of Chi Shao, 3 parts of Sha Ren, 2 parts of Cao Dou Kou, 2 parts of Tu Mu Xiang, 2 parts of Da Huang and 2 parts of Shan Yao was prepared and formed into oral solutions.

A method for preparing the pharmaceutical composition included the steps of:

A) subjecting a first group of TCM materials including Gan Jiang, Sha Ren, Cao Dou Kou, and Tu Mu Xiang to three reflux extraction processes each lasting for 1 hour and using a 50% ethanol solution as an extraction medium which had the number of liters 7 times the number of kilograms of the first group of TCM materials;

B) combining and filtering the ethanol solutions used in the three reflux extraction processes and concentrating the filtrate under a reduced pressure, concurrently with recovery of the ethanol, until its relative density came to 1.05-1.15 (measured at 60° C.);

C) subjecting a second group of TCM materials including Chi Shao, Da Huang, Shan Yao to three boiling processes each lasting for 1 hour and using water with a weight 9 times the total weight of the second group of TCM materials as a boil medium;

D) combining and filtering the water used in the three boiling processes, mixing the filtrate with the filtrate obtained from step B, concentrating the mixture until its weight was 1.5 times the total weight of the first and second groups of TCM materials and keeping the concentrate at room temperature for 24 hours; and E) filtering and centrifuging the supernatant of the concentrate and concentrating the centrifugate into an extract with a relative density of 1.15-1.20 (60° C.), followed by dosing and bottling thereof.

Optionally, Zhi Shi, Huang Qin and Zhu Ru can be added in the above pharmaceutical composition for treating eczema according to the following weight ratio: 4 parts of Gan Jiang, 4 parts of Zhi Shi, 4 parts of Chi Shao, 3 parts of Sha Ren, 2 parts of Cao Dou Kou, 2 parts of Huang Qin, 2 parts of Tu Mu Xiang, 2 parts of Da Huang, 2 parts of Shan Yao and 2 parts of Zhu Ru.

Correspondingly, in the above preparation method, the method further optionally includes adding Zhi Shi and Huang Qin to the first group of TCM materials in step A and adding Zhu Ru to the second group of TCM materials in step C according to the above weight ratio.

EXAMPLE 3

A pharmaceutical composition for treating eczema, including, by weight, 4.5 parts of Gan Jiang, 4.5 parts of Chi Shao, 3 parts of Sha Ren, 1.5 parts of Cao Dou Kou, 1.5 parts of Tu Mu Xiang, 1.5 parts of Da Huang and 1.5 parts of Shan Yao was prepared and formed into granules.

A method for preparing the pharmaceutical composition included the steps of:

A) subjecting a first group of TCM materials including Gan Jiang, Sha Ren, Cao Dou Kou and Tu Mu Xiang to three reflux extraction processes each lasting for 1.5 hours and using a 65% ethanol solution as an extraction medium which had the number of liters 8 times the number of kilograms of the first group of TCM materials;

B) combining and filtering the ethanol solutions used in the three reflux extraction processes and concentrating the filtrate under a reduced pressure, concurrently with recovery of the ethanol, until its relative density came to 1.05-1.15 (measured at 60° C.);

C) subjecting a second group of TCM materials including Chi Shao, Da Huang and Shan Yao to three boiling processes each lasting for 1.5 hours and using water with a weight 10 times the total weight of the second group of TCM materials as a boil medium;

D) combining and filtering the water used in the three boiling processes, mixing the filtrate with the filtrate obtained from step B, concentrating the mixture until its weight was 1.5 times the total weight of the first and second groups of TCM materials and keeping the concentrate at room temperature for 24 hours;

E) filtering and centrifuging the supernatant of the concentrate, concentrating the centrifugate into an extract with a relative density of 1.25-1.35 (60° C.), and drying with microwaves and pulverizing the extract; and F) homogeneously mixing the pulverized extract with starch, forming the mixture into granules and filling the granules in packs.

Optionally, Zhi Shi, Huang Qin and Zhu Ru can be added in the above pharmaceutical composition for treating eczema according to the following weight ratio: 4.5 parts of Gan Jiang, 4.5 parts of Zhi Shi, 4.5 parts of Chi Shao, 3 parts of Sha Ren, 1.5 parts of Cao Dou Kou, 1.5 parts of Huang Qin, 1.5 parts of Tu Mu Xiang, 1.5 parts of Da Huang, 1.5 parts of Shan Yao and 1.5 parts of Zhu Ru.

Correspondingly, in the above preparation method, the method further optionally includes adding Zhi Shi and Huang Qin to the first group of TCM materials in step A and adding Zhu Ru to the second group of TCM materials in step C according to the above weight ratio.

EXAMPLE 4

A pharmaceutical composition for treating eczema, including, by weight, 3 parts of Gan Jiang, 3 parts of Chi Shao, 2 parts of Sha Ren, 1 part of Cao Dou Kou, 1 part of Tu Mu Xiang, 1 part of Da Huang and 1 part of Shan Yao was prepared and formed into tablets.

A method for preparing the pharmaceutical composition included the steps of:

A) subjecting a first group of TCM materials including Gan Jiang, Sha Ren, Cao Dou Kou and Tu Mu Xiang to three reflux extraction processes each lasting for 1.5 hours and using a 65% ethanol solution as an extraction medium which had the number of liters 8 times the number of kilograms of the first group of TCM materials;

B) combining and filtering the ethanol solutions used in the three reflux extraction processes and concentrating the filtrate under a reduced pressure, concurrently with recovery of the ethanol, until its relative density came to 1.05-1.15 (measured at 60° C.);

C) subjecting a second group of TCM materials including Chi Shao, Da Huang and Shan Yao to three boiling processes each lasting for 1.5 hours and using water with a weight 10 times the total weight of the second group of TCM materials as a boil medium;

D) combining and filtering the water used in the three boiling processes, mixing the filtrate with the filtrate obtained from step B, concentrating the mixture until its weight was 1.5 times the total weight of the first and second groups of TCM materials and keeping the concentrate at room temperature for 24 hours;

E) filtering and centrifuging the supernatant of the concentrate, concentrating the centrifugate into an extract with a relative density of 1.20-1.30 (60° C.), and drying with microwaves and pulverizing the extract; and F) homogeneously mixing the pulverized extract with starch, forming the mixture into granules and filling the granules in capsules.

Optionally, Zhi Shi, Huang Qin and Zhu Ru can be added in the above pharmaceutical composition for treating eczema according to the following weight ratio: 3 parts of Gan Jiang, 3 parts of Zhi Shi, 3 parts of Chi Shao, 2 parts of Sha Ren, 1 part of Cao Dou Kou, 1 part of Huang Qin, 1 part of Tu Mu Xiang, 1 part of Da Huang, 1 part of Shan Yao and 1 part of Zhu Ru.

Correspondingly, in the above preparation method, the method further optionally includes adding Zhi Shi and Huang Qin to the first group of TCM materials in step A and adding Zhu Ru to the second group of TCM materials in step C according to the above weight ratio.

EXAMPLE 5

A pharmaceutical composition for treating eczema, including, in every 12 g of it, 3 g of Gan Jiang, 3 g of Chi Shao, 2 g of Sha Ren, 1 g of Cao Dou Kou, 1 g of Tu Mu Xiang, 1 g of Da Huang and 1 g of Shan Yao was prepared and formed into capsules.

A method for preparing the pharmaceutical composition included the steps of:

A) subjecting a first group of TCM materials including Gan Jiang, Sha Ren, Cao Dou Kou and Tu Mu Xiang to three reflux extraction processes each lasting for 1.5 hours and using a 70% ethanol solution as an extraction medium which had the number of liters 8 times the number of kilograms of the first group of TCM materials;

B) combining and filtering the ethanol solutions used in the three reflux extraction processes and concentrating the filtrate under a reduced pressure, concurrently with recovery of the ethanol, until its relative density came to 1.05-1.15 (measured at 60° C.);

C) subjecting a second group of TCM materials including Chi Shao, Da Huang and Shan Yao to three boiling processes each lasting for 1.5 hours and using water with a weight 10 times the total weight of the second group of TCM materials as a boil medium;

D) combining and filtering the water used in the three boiling processes, mixing the filtrate with the filtrate obtained from step B, concentrating the mixture until its weight was 1.5 times the total weight of the first and second groups of TCM materials and keeping the concentrate at room temperature for 24 hours;

E) filtering and centrifuging the supernatant of the concentrate, concentrating the centrifugate into an extract with a relative density of 1.20-1.30 (60° C.), and drying with microwaves and pulverizing the extract; and F) homogeneously mixing the pulverized extract with starch, forming the mixture into granules and filling the granules in packs.

Optionally, Zhi Shi, Huang Qin and Zhu Ru can be added in the above pharmaceutical composition for treating eczema, such that the pharmaceutical composition includes, in every 17 g of it, 3 g of Gan Jiang, 3 g of Zhi Shi, 3 g of Chi Shao, 2 g of Sha Ren, 1 g of Cao Dou Kou, 1 g of Huang Qin, 1 g of Tu Mu Xiang, 1 g of Da Huang, 1 g of Shan Yao and 1 g of Zhu Ru.

Correspondingly, in the above preparation method, the method further optionally includes adding Zhi Shi and Huang Qin to the first group of TCM materials in step A and adding Zhu Ru to the second group of TCM materials in step C according to the above weight ratio.

EXAMPLE 6

A pharmaceutical composition for treating eczema, including, in every 12 g of it, 3 g of Gan Jiang, 3 g of Chi Shao, 2 g of Sha Ren, 1 g of Cao Dou Kou, 1 g of Tu Mu Xiang, 1 g of Da Huang and 1 g of Shan Yao was prepared and formed into dropping pills.

A method for preparing the pharmaceutical composition included the steps of:

A) subjecting a first group of TCM materials including Gan Jiang, Sha Ren, Cao Dou Kou and Tu Mu Xiang to three reflux extraction processes each lasting for 1 hour and using a 75% ethanol solution as an extraction medium which had the number of liters 9 times the number of kilograms of the first group of TCM materials;

B) combining and filtering the ethanol solutions used in the three reflux extraction processes and concentrating the filtrate under a reduced pressure, concurrently with recovery of the ethanol, until its relative density came to 1.05-1.15 (measured at 60° C.);

C) subjecting a second group of TCM materials including Chi Shao, Da Huang and Shan Yao to three boiling processes each lasting for 1 hour and using water with a weight 12 times the total weight of the second group of TCM materials as a boil medium;

D) combining and filtering the water used in the three boiling processes, mixing the filtrate with the filtrate obtained from step B, concentrating the mixture until its weight was 2 times the total weight of the first and second groups of TCM materials and keeping the concentrate at room temperature for 24 hours; and E) filtering and centrifuging the supernatant of the concentrate and concentrating the centrifugate into an extract with a relative density of 1.25-1.35 (60° C.), following by dosing and formation of the extract into dropping pills.

Optionally, Zhi Shi, Huang Qin and Zhu Ru can be added in the above pharmaceutical composition for treating eczema, such that the pharmaceutical composition includes, in every 17 g of it, 3 g of Gan Jiang, 3 g of Zhi Shi, 3 g of Chi Shao, 2 g of Sha Ren, 1 g of Cao Dou Kou, 1 g of Huang Qin, 1 g of Tu Mu Xiang, 1 g of Da Huang, 1 g of Shan Yao and 1 g of Zhu Ru.

Correspondingly, in the above preparation method, the method further optionally includes adding Zhi Shi and Huang Qin to the first group of TCM materials in step A and adding Zhu Ru to the second group of TCM materials in step C according to the above weight ratio.

EXAMPLE 7

A pharmacodynamic study was conducted to investigate immune effects of eczema-treating pharmaceutical compositions.

1 Materials and Methods 1.1 Test drugs: Capsules of an eczema-treating pharmaceutical composition prepared from 7 TCM materials in accordance with Example 5 (Capsules A), capsules of an eczema-treating pharmaceutical composition prepared from the 10 TCM, materials in accordance with Example 5 (Capsules B) and Kushen Capsules (as a positive control drug containing Sophorae flavescentis radix (Kushen) as the main TCM material).

1.2 Reagents: dinitrochlorobenzene (DNCB), eosinophil cationic protein (ECP), ELISA kits, different fluorescein-labelled anti-CD4 and anti-CD8 (anti-CD4/CD8) monoclonal antibodies.

1.3 Animals: 30 male and 30 female healthy guinea pigs from the Experimental Animal Center each with a body weight of 250-300 g.

1.4 Instruments: a Biochrom. EZ Read 400 ELISA microplate reader and a Gallios flow cytometer.

1.5 Methods 1.5.1 Modeling: Models for acute eczema were made. The guinea pigs' necks were depilated one day before the start of the study and each applied with 25 μl of a 5% acetone solution of DNCB for allergization on the day of the study. One week later, 100 μl of a 1% acetone solution of DNCB was applied as a stimulus on the inner side of the right ear of each of the guinea pigs. Subsequently, this was repeated for five times at an interval of 3 days. Each of the guinea pigs was determined as being usable as a model for acute eczema if it had been observed to have an obvious red and swollen right ear with oozing and crusting compared with its left ear.

1.5.2 Grouping: the 60 guinea pigs were randomly and equally divided into the following 6 groups (i.e., 10 in each group): blank control (hereinafter referred to as "Blank Group"); models for acute eczema as blank control ("Model Group"); models for acute eczema administrated with a low dose of the capsules A ("Low-Dose Group A"); models for acute eczema administrated with a high dose of the capsules A ("High-Dose Group"); models for acute eczema administrated with a low dose of the capsules B ("Low-Dose Group B"); and models for acute eczema as positive control ("Positive Control Group").

1.5.3 Administration: One day after the last application of the stimulus, Positive Control Group was intragastrically given 0.46 g/kg of Kushen Capsules, Low-Dose Group B intragastrically 0.46 g/kg of Capsules B, Low-Dose Group A intragastrically 0.46 g/kg of Capsules A, High-Dose Group intragastrically 1.84 g/kg of Capsules A, and both Blank and Model Groups intragastrically a normal saline, once every day continuously for two weeks.

1.5.4 Indicators and Assays 1.5.4.1 Serum ECP Level After two weeks of continuous administration, blood samples were collected from the abdominal aortas of the guinea pigs and centrifuged. Serums were taken and subjected to ELISA assays for determination of ECP levels therein.

1.5.4.2 $CD4^+$ and $CD8^+$ T Lymphocyte Levels Subsequent to two weeks of continuous administration, 2 ml of whole blood was collected from each of the guinea pigs through heart puncture 2 h after the last administration and added with heparin for full anticoagulation. Each anticoagulated blood sample was transferred carefully with a glass capillary pipette onto 2 ml of a lymphocyte separation medium contained in a test tube so that it slowly flowed down along the wall of the test tube, resulting in a clear interface between the two liquids. The test tube was then subjected to centrifugation at 2000 rpm for 10 min. The resulting lymphocyte layer at the interface, together with the serum, was drawn into a glass capillary pipette and added into another scaled centrifuge tube and rinsed with PBS buffer for three times. The lymphocyte concentration was conditioned to $10^5$/mL during the last rinsing cycle, and 0.5 ml of the lymphocyte suspension was taken, added with 5 μl of a doubly-labelled antibody, mixed well, incubated in a dark location at 37° C. for 30 min, rinsed with PBS buffer for twice and tested.

2 Results 2.1 Effect of the eczema-treating pharmaceutical compositions according to the present invention on serum ECP levels of the guinea pigs Guinea pigs in Model Group had higher serum ECP levels than the Blank Group ones (P<0.01), indicating the success of the modeling. Compared to Model Group, High-Dose Group, Low-Dose Group A, Low-Dose Group B and Positive Control Group all had significantly reduced serum ECP levels (P<0.05 or P<0.01). High-Dose Group exhibited a better therapeutic effect than Low-Dose Group A, Low-Dose Group B, and Positive Control Group (P<0.05). Low-Dose Group A exhibited a better therapeutic effect than Low-Dose Group B and Positive Control Group, but the difference was not statistically significant (P>0.05). These results are shown in Table 1.

TABLE 1

Effects of the capsules of the compositions on serum ECP levels of the guinea pigs ($\bar{x} \pm s$, n = 10)

| Group | Dose (g/kg) | ECP (ng/ml) |
|---|---|---|
| Blank | — | 4.97 ± 0.57 |
| Model | — | 8.45 ± 0.63** |
| High-Dose | 1.84 | 5.46 ± 0.47## |
| Low-Dose A | 0.46 | 6.68 ± 0.58#Δ |
| Low-Dose B | 0.46 | 6.87 ± 0.59#Δ |
| Positive Control | 0.46 | 6.72 ± 0.53#Δ |

Note:
Compare with Blank Group, **P < 0.01; compare with Model Group, ##P < 0.01 and #P < 0.05; and compare with High-Dose Group, ΔP < 0.05.

2.2 Effect of the eczema-treating pharmaceutical compositions according to the present invention on $CD4^+$ and $CD8^+$ T lymphocyte levels of the guinea pigs as well as on their ratios The $CD4^+$ T lymphocyte levels of Model Group were statistically significantly (P<0.01) lower than those of Blank Group. While the $CD4^+$ T lymphocyte levels of the therapeutic groups were averagely higher than those of Model Group, only High-Dose Group showed a statistical difference (P<0.05). The $CD8^+$ F lymphocyte levels of Model Group were statistically significantly (P<0.01) higher than those of Blank Group. While the $CD8^+$ F lymphocyte levels of the therapeutic groups were averagely lower than those of Model Group, only High-Dose Group showed a statistical difference (P<0.05). The CD4$^+$/CD8$^+$ ratios of Model Group were statistically significantly (P<0.01) lower than those of Blank Group. While the CD4$^+$/CD8$^+$ ratios of the therapeutic groups were higher than those of Model Group, only High-Dose Group showed a statistical difference (P<0.05). These results are summarized in Table 2.

TABLE 2

Effects of the capsules of the compositions on CD4$^+$ and CD8$^+$ T Lymphocyte Levels and CD4$^+$/CD8$^+$ ratios of the guinea pigs ($\bar{x} \pm s$, n = 10)

| Group | CD4$^+$ | CD8$^+$ | CD4$^+$/CD8$^+$ |
|---|---|---|---|
| Blank | 38.57 ± 1.41 | 16.98 ± 1.25 | 2.27 ± 0.25 |
| Model | 27.56 ± 3.67** | 26.11 ± 3.89** | 1.06 ± 0.49** |
| High-Dose | 32.83 ± 3.58# | 19.93 ± 4.43# | 1.65 ± 0.37# |
| Low-Dose A | 30.74 ± 4.13 | 22.86 ± 3.11 | 1.34 ± 0.31 |
| Low-Dose B | 29.51 ± 3.67 | 23.42 ± 4.52 | 1.26 ± 0.48 |
| Positive Control | 29.72 ± 3.72 | 23.13 ± 4.65 | 1.28 ± 0.45 |

Note:
Compare with Blank Group, **P < 0.01; and compare with Model Group, #P < 0.05.

While the present invention has been described above with reference to several preferred embodiments, they are not intended to limit the invention in any sense. Those of ordinary skill in the art can make various changes and modifications without departing from the spirit and scope of the invention. Accordingly, the scope of the invention is intended to be defined by the appended claims.

What is claimed is:

1. A pharmaceutical composition for treating eczema, comprising, by weight, 2 to 6 parts of Dried Rhizoma Zingiberis Officinalis, 2 to 6 parts of Paeonia Lactiflora, 1 to 4 parts of Fructus Amomi, 0.5 to 3 parts of Semen Alpiniae Katsumadai, 0.5 to 3 parts of Inula helenium, 0.5 to 3 parts of Radix Et Rhizoma Rhei, 0.5 to 3 parts of Rhizoma Dioscoreae, 2 to 6 parts of Fructus Aurantii Immaturus, 0.5 to 3 parts of Radix Scutellariae Baicalensis and 0.5 to 3 parts of Caulis Bambusae in Taeniam.

2. The pharmaceutical composition for treating eczema according to claim 1, comprising, by weight, 2 to 4 parts of Dried Rhizoma Zingiberis Officinalis, 2 to 4 parts of Paeonia Lactiflora, 1 to 3 parts of Fructus Amomi, 0.5 to 2 parts of Semen Alpiniae Katsumadai, 0.5 to 2 parts of Inula helenium, 0.5 to 2 parts of Radix Et Rhizoma Rhei, 0.5 to 2 parts of Rhizoma Dioscoreae, 2 to 4 parts of Fructus Aurantii Immaturus, 0.5 to 2 parts of Radix Scutellariae Baicalensis and 0.5 to 2 parts of Caulis Bambusae in Taeniam.

3. The pharmaceutical composition for treating eczema according to claim 2, comprising, by weight, 3 parts of Dried Rhizoma Zingiberis Officinalis, 3 parts of Paeonia Lactiflora, 2 parts of Fructus Amomi, 1 part of Semen Alpiniae Katsumadai, 1 part of Inula helenium, 1 part of Radix Et Rhizoma Rhei, 1 part of Rhizoma Dioscoreae, 3 parts of Fructus Aurantii Immaturus, 1 part of Radix Scutellariae Baicalensis and 1 part of Caulis Bambusae in Taeniam.

4. The pharmaceutical composition for treating eczema according to claim 1, comprising, in every 17 g of the pharmaceutical composition, 3 g of Dried Rhizoma Zingiberis Officinalis, 3 g of Paeonia Lactiflora, 2 g of Fructus Amomi, 1 g of Semen Alpiniae Katsumadai, 1 g of Inula helenium, 1 g of Radix Et Rhizoma Rhei, 1 g of Rhizoma Dioscoreae, 3 g of Fructus Aurantii Immaturus, 1 g of Radix Scutellariae Baicalensis and 1 g of Caulis Bambusae in Taeniam.

5. The pharmaceutical composition for treating eczema according to claim 1, wherein the pharmaceutical composition is in a form of oral solutions, tablets, capsules, pills granules or dropping pills.

6. A method for preparing the pharmaceutical composition for treating eczema according to claim 1, comprising:
   step A) subjecting a first group of medicine materials including Dried Rhizoma Zingiberis Officinalis, Fructus Amomi, Semen Alpiniae Katsumadai, Fructus Aurantii Immaturus and Radix Scutellariae Baicalensis and Inula helenium to three reflux extraction processes each lasting for 1-2 hours and using a 50%-80% ethanol solution as an extraction medium which has a number of units of volume (L) 6 times a number of units of a total weight (Kg) of the first group of medicine materials;
   step B) combining and filtering the ethanol solutions used in the three reflux extraction processes to obtain a first filtrate and concentrating the first filtrate under a reduced pressure, concurrently with recovery of the ethanol solutions, until relative density of the concentrated first filtrate comes to 1.05-1.15;
   step C) subjecting a second group of medicine materials including Paeonia Lactiflora, Radix Et Rhizoma Rhei Caulis Bambusae in Taeniam and Rhizoma Dioscoreae to three boiling processes each lasting for 1-2 hours and using water with a weight 8-12 times a total weight of the second group of medicine materials as a boil medium;
   step D) combining and filtering the water used in the three boiling processes to obtain a second filtrate, mixing the second filtrate with the first filtrate obtained from step B to obtain a first mixture, concentrating the first mixture until a weight of the first mixture becomes 1-3 times a total weight of the first and second groups of medicine materials and keeping the concentrated first mixture at room temperature for 24 hours; and
   step E) filtering and centrifuging a supernatant of the concentrated first mixture to obtain a centrifugate, concentrating the centrifugate into an extract with a relative density of 1.10-1.35, and drying the extract to produce the pharmaceutical composition.

7. The method according to claim 6, further comprising: step F) homogeneously mixing the pharmaceutical composition with starch to obtain a second mixture, forming the second mixture into granules and filling the granules in packs.

8. The method according to claim 6, wherein in step B, the first filtrate is concentrated at 75° C. until the relative density of the concentrated first filtrate comes to 1.05-1.15.

9. The method according to claim 6, wherein in step E, the centrifugate is concentrated at 75° C. into the extract with a relative density of 1.10-1.35, and the extract is dried with microwaves to produce the pharmaceutical composition.

* * * * *